US012582475B2

(12) United States Patent
Upadrasta et al.

(10) Patent No.: US 12,582,475 B2
(45) Date of Patent: Mar. 24, 2026

(54) HYBRID SIMULATION MODEL FOR SIMULATING MEDICAL PROCEDURES

(71) Applicant: Intuitive Surgical Operations, Inc., Sunnyvale, CA (US)

(72) Inventors: Prasad V. Upadrasta, San Jose, CA (US); Joey Chau, Cupertino, CA (US); May Quo-Mei Liu, Hillsborough, NC (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 931 days.

(21) Appl. No.: 17/254,906

(22) PCT Filed: Jun. 25, 2019

(86) PCT No.: PCT/US2019/038911
§ 371 (c)(1),
(2) Date: Dec. 22, 2020

(87) PCT Pub. No.: WO2020/005890
PCT Pub. Date: Jan. 2, 2020

(65) Prior Publication Data
US 2021/0259776 A1     Aug. 26, 2021

Related U.S. Application Data

(60) Provisional application No. 62/689,584, filed on Jun. 25, 2018.

(51) Int. Cl.
*G01N 33/48*     (2006.01)
*A61B 34/00*     (2016.01)
(Continued)

(52) U.S. Cl.
CPC .............. *A61B 34/10* (2016.02); *A61B 34/25* (2016.02); *A61B 2034/104* (2016.02);
(Continued)

(58) Field of Classification Search
CPC ... A61B 34/10; A61B 34/25; A61B 2034/104; A61B 2034/105; A61B 2034/107; A61B 2034/256
See application file for complete search history.

(56) References Cited

U.S. PATENT DOCUMENTS

2017/0209071 A1     7/2017   Zhao et al.
2017/0216121 A1*    8/2017   White ................... A61G 13/12
2017/0312031 A1     11/2017  Amanatullah et al.

FOREIGN PATENT DOCUMENTS

CN            102346811 A      2/2012
WO       WO-2016018646 A1      2/2016
WO       WO-2019119297 A1 *    6/2019   ............. A61B 34/37

OTHER PUBLICATIONS

Pettersson et al. Simulation of patient specific cervical hip fracture surgery with a vol. haptic interface. IEEE Transactions on Biomedical Engineering, vol. 55, pp. 1255-1265. (Year: 2008).*
(Continued)

*Primary Examiner* — Russell S Negin
(74) *Attorney, Agent, or Firm* — Haynes & Boone, LLP.

(57)     ABSTRACT

A method and apparatus for simulating a medical procedure to be performed on a patient. Patient-specific data that is specific to the patient on whom the medical procedure is to be performed is received. A generic model is modified using the patient-specific data to generate a hybrid simulation model that is customized to the patient. A simulation of the medical procedure is performed using the hybrid simulation model and dynamic simulation information corresponding to at least one of the medical procedure or the patient. The
(Continued)

simulation is customized to both the patient and the medical procedure.

27 Claims, 8 Drawing Sheets

(51) Int. Cl.
    *A61B 34/10*              (2016.01)
    *G01N 33/50*          (2006.01)

(52) U.S. Cl.
    CPC ... *A61B 2034/105* (2016.02); *A61B 2034/107*
                (2016.02); *A61B 2034/256* (2016.02)

(56) References Cited

OTHER PUBLICATIONS

English machine translation of WO 2019/119297A1. (Year: 2025).*
International Preliminary Report on Patentability for Application No. PCT/2019/038911, mailed on Jan. 7, 2021, 09 pages.
International Search Report and Written Opinion for Application No. PCT/US2019/038911. mailed on Sep. 23, 2019, 14 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

228

600

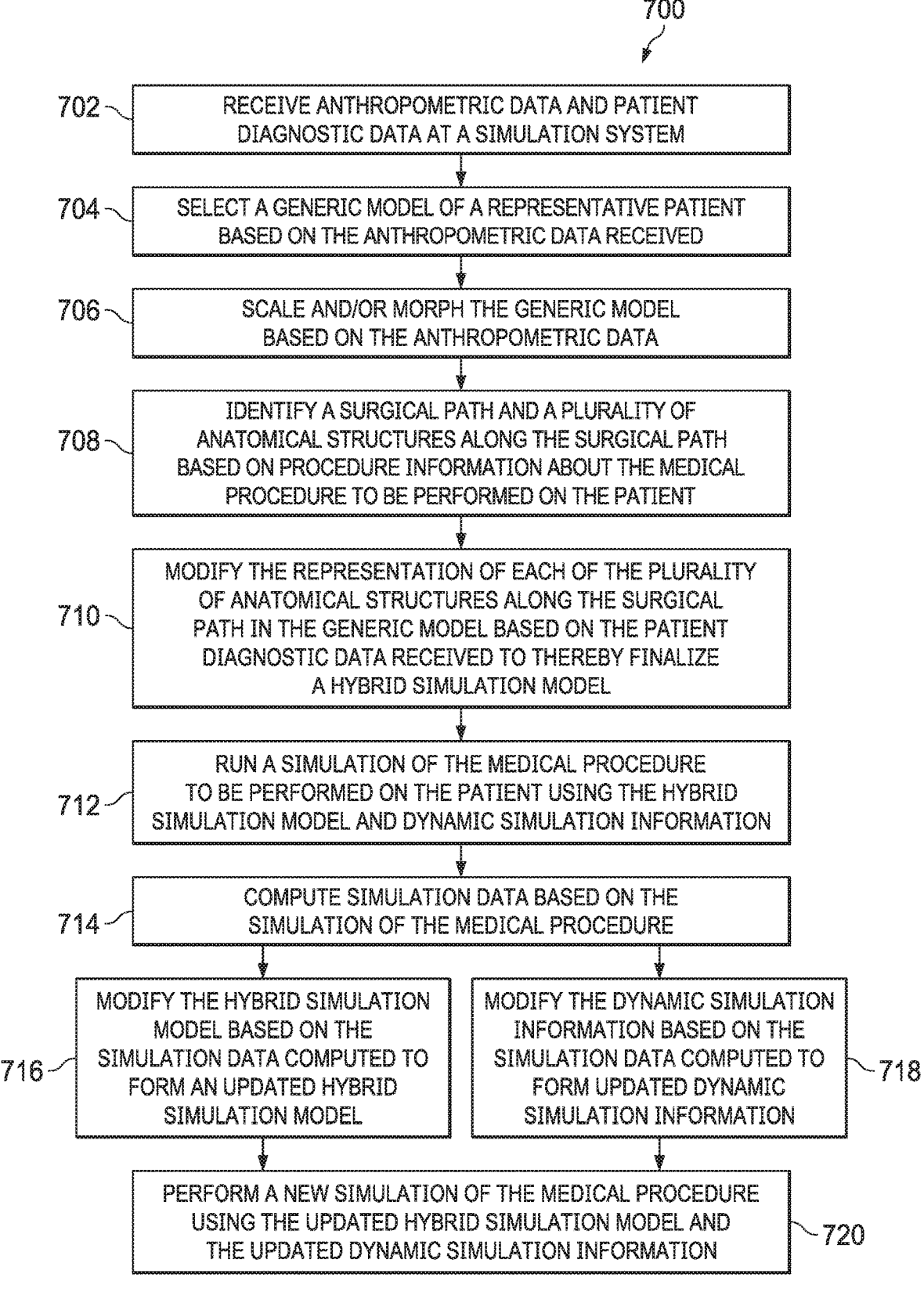

700

702 — RECEIVE ANTHROPOMETRIC DATA AND PATIENT DIAGNOSTIC DATA AT A SIMULATION SYSTEM

704 — SELECT A GENERIC MODEL OF A REPRESENTATIVE PATIENT BASED ON THE ANTHROPOMETRIC DATA RECEIVED

706 — SCALE AND/OR MORPH THE GENERIC MODEL BASED ON THE ANTHROPOMETRIC DATA

708 — IDENTIFY A SURGICAL PATH AND A PLURALITY OF ANATOMICAL STRUCTURES ALONG THE SURGICAL PATH BASED ON PROCEDURE INFORMATION ABOUT THE MEDICAL PROCEDURE TO BE PERFORMED ON THE PATIENT

710 — MODIFY THE REPRESENTATION OF EACH OF THE PLURALITY OF ANATOMICAL STRUCTURES ALONG THE SURGICAL PATH IN THE GENERIC MODEL BASED ON THE PATIENT DIAGNOSTIC DATA RECEIVED TO THEREBY FINALIZE A HYBRID SIMULATION MODEL

712 — RUN A SIMULATION OF THE MEDICAL PROCEDURE TO BE PERFORMED ON THE PATIENT USING THE HYBRID SIMULATION MODEL AND DYNAMIC SIMULATION INFORMATION

714 — COMPUTE SIMULATION DATA BASED ON THE SIMULATION OF THE MEDICAL PROCEDURE

716 — MODIFY THE HYBRID SIMULATION MODEL BASED ON THE SIMULATION DATA COMPUTED TO FORM AN UPDATED HYBRID SIMULATION MODEL

MODIFY THE DYNAMIC SIMULATION INFORMATION BASED ON THE SIMULATION DATA COMPUTED TO FORM UPDATED DYNAMIC SIMULATION INFORMATION — 718

PERFORM A NEW SIMULATION OF THE MEDICAL PROCEDURE USING THE UPDATED HYBRID SIMULATION MODEL AND THE UPDATED DYNAMIC SIMULATION INFORMATION — 720

Fig. 7

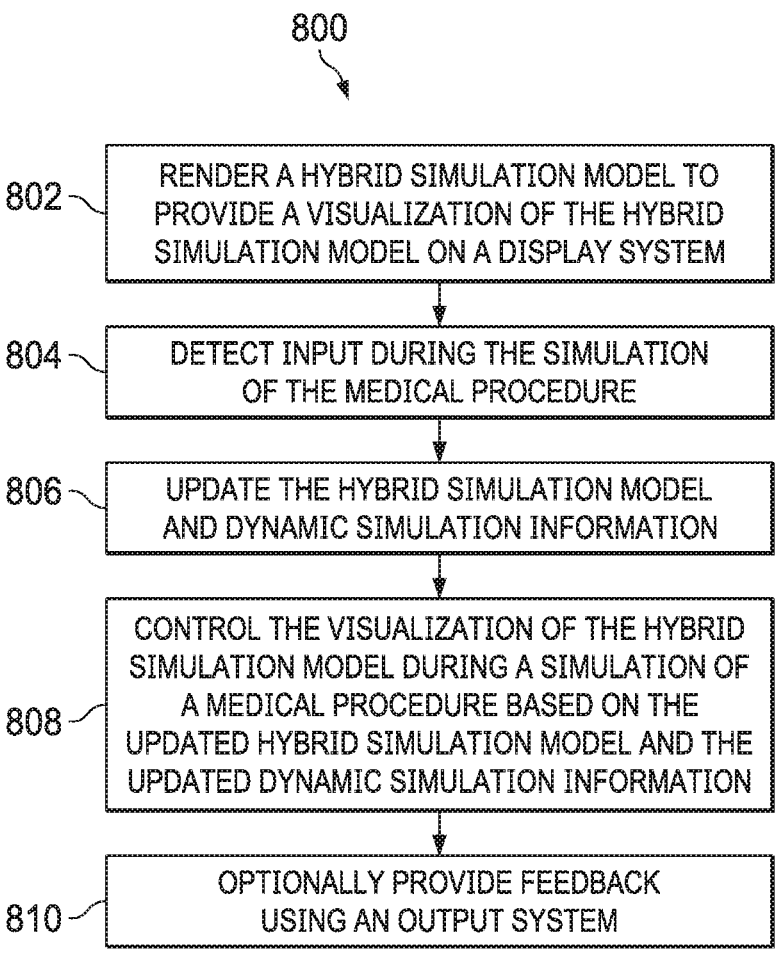

800

802 — RENDER A HYBRID SIMULATION MODEL TO PROVIDE A VISUALIZATION OF THE HYBRID SIMULATION MODEL ON A DISPLAY SYSTEM

804 — DETECT INPUT DURING THE SIMULATION OF THE MEDICAL PROCEDURE

806 — UPDATE THE HYBRID SIMULATION MODEL AND DYNAMIC SIMULATION INFORMATION

808 — CONTROL THE VISUALIZATION OF THE HYBRID SIMULATION MODEL DURING A SIMULATION OF A MEDICAL PROCEDURE BASED ON THE UPDATED HYBRID SIMULATION MODEL AND THE UPDATED DYNAMIC SIMULATION INFORMATION

810 — OPTIONALLY PROVIDE FEEDBACK USING AN OUTPUT SYSTEM

Fig. 8

HYBRID SIMULATION MODEL FOR SIMULATING MEDICAL PROCEDURES

CROSS-REFERENCE TO RELATED APPLICATIONS

This application is the U.S. national phase of International Application No. PCT/US2019/38911, filed Jun. 25, 2019, which designates the U.S. and claims priority to and the benefit of U.S. Provisional Application No. 62/689,584, filed Jun. 25, 2018, both of which are incorporated by reference herein in their entirety.

FIELD

The present disclosure is directed to medical procedures and methods for simulating minimally invasive medical procedures. More particularly, the present disclosure is directed to systems and methods for providing a hybrid simulation model that has been customized to a particular patient and a particular medical procedure that is to be performed on the patient.

BACKGROUND

Minimally invasive medical techniques are intended to reduce the amount of extraneous tissue that is damaged during diagnostic or surgical procedures, thereby reducing patient recovery time, discomfort, and harmful side effects. Such minimally invasive techniques may be performed through natural orifices in a patient anatomy or through one or more surgical incisions. Through these natural orifices or incisions, clinicians may insert medical tools to reach a target tissue location. Minimally invasive medical tools include instruments such as therapeutic instruments, diagnostic instruments, and surgical instruments. Minimally invasive medical tools may also include imaging instruments such as endoscopic instruments that provide a user with a field of view within the patient anatomy.

Some minimally invasive medical tools may be teleoperated, otherwise remotely operated, or otherwise computer-assisted. A clinician near a teleoperational system may need to receive guidance in the form of instructions, warnings, confirmations, or the like before, during, or after a medical procedure performed with the teleoperational system. Systems and methods for improving the process of generating simulation models that are used to simulate the medical procedure are needed.

SUMMARY

The embodiments of the invention are summarized by the claims that follow below.

In an embodiment, a method is provided for simulating a medical procedure to be performed on a patient. Patient-specific data that is specific to the patient on whom the medical procedure is to be performed is received. A generic model is modified using the patient-specific data to generate a hybrid simulation model that is customized to the patient. A simulation of the medical procedure is performed using the hybrid simulation model and dynamic simulation information corresponding to at least one of the medical procedure or the patient. The simulation is customized to both the patient and the medical procedure.

In another embodiment, a simulation system comprises a computer system configured to receive patient-specific data that is specific to a patient on whom a medical procedure is to be performed; modify a generic model using the patient-specific data to generate a hybrid simulation model that is customized to the patient. The computer system is configured to perform a simulation of the medical procedure using the hybrid simulation model and dynamic simulation information corresponding to at least one of the medical procedure or the patient, wherein the simulation is customized to both the patient and the medical procedure.

In yet another embodiment, a method for simulating a medical procedure to be performed on a patient is provided. Anthropometric data and patient diagnostic data are received for the patient. A generic model of a representative patient is selected from a database system. The generic model is modified based on the anthropometric data and the patient diagnostic data to generate a hybrid simulation model that is customized to the patient. A simulation of the medical procedure is performed using the hybrid simulation model and dynamic simulation information corresponding to at least one of the medical procedure or the patient. The simulation is customized to both the patient and the medical procedure. The simulation accounts for effects of simulated interactions between anatomical structures of the patient and instruments used in the medical procedure. The simulation dynamically adapts to each step of the medical procedure such that a portion of the patient anatomy that interacts with the medical procedure at each step is rendered at a higher level of fidelity.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 7 is a flowchart illustration of a method for generating a hybrid simulation model for use in simulating a medical procedure that is to be performed on a patient, in accordance with an embodiment.

Figure 1A:
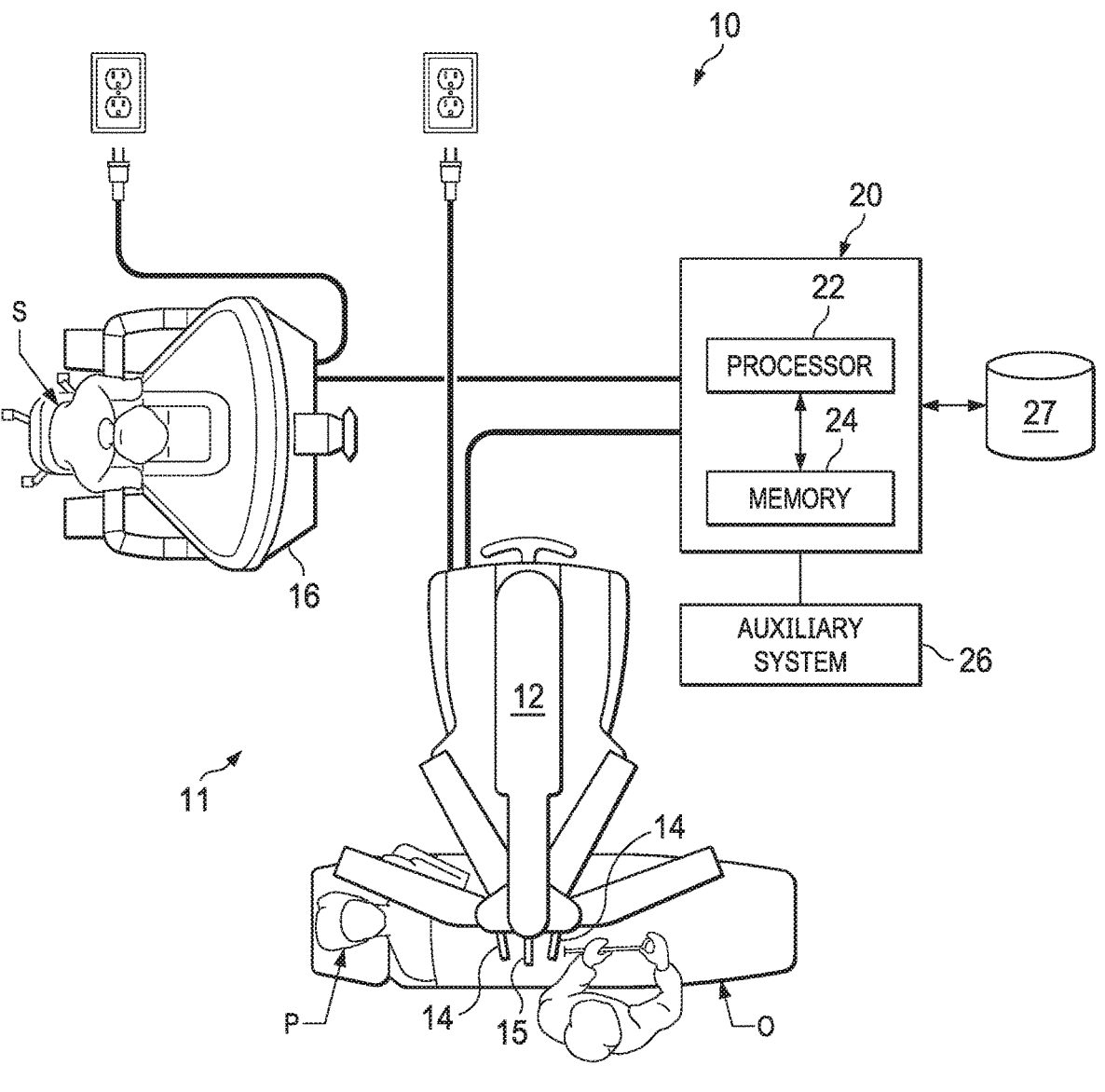
FIG. 1A is a schematic view of a medical system, in accordance with an embodiment.

FIG. 8 a flowchart illustration of a method for running a simulation of a medical procedure using a hybrid simulation model, in accordance with an embodiment.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, as would be appreciated by one skilled in the art, embodiments of this disclosure may be practiced without these specific details. In other instances, well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment may be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom).

Figure 1B:
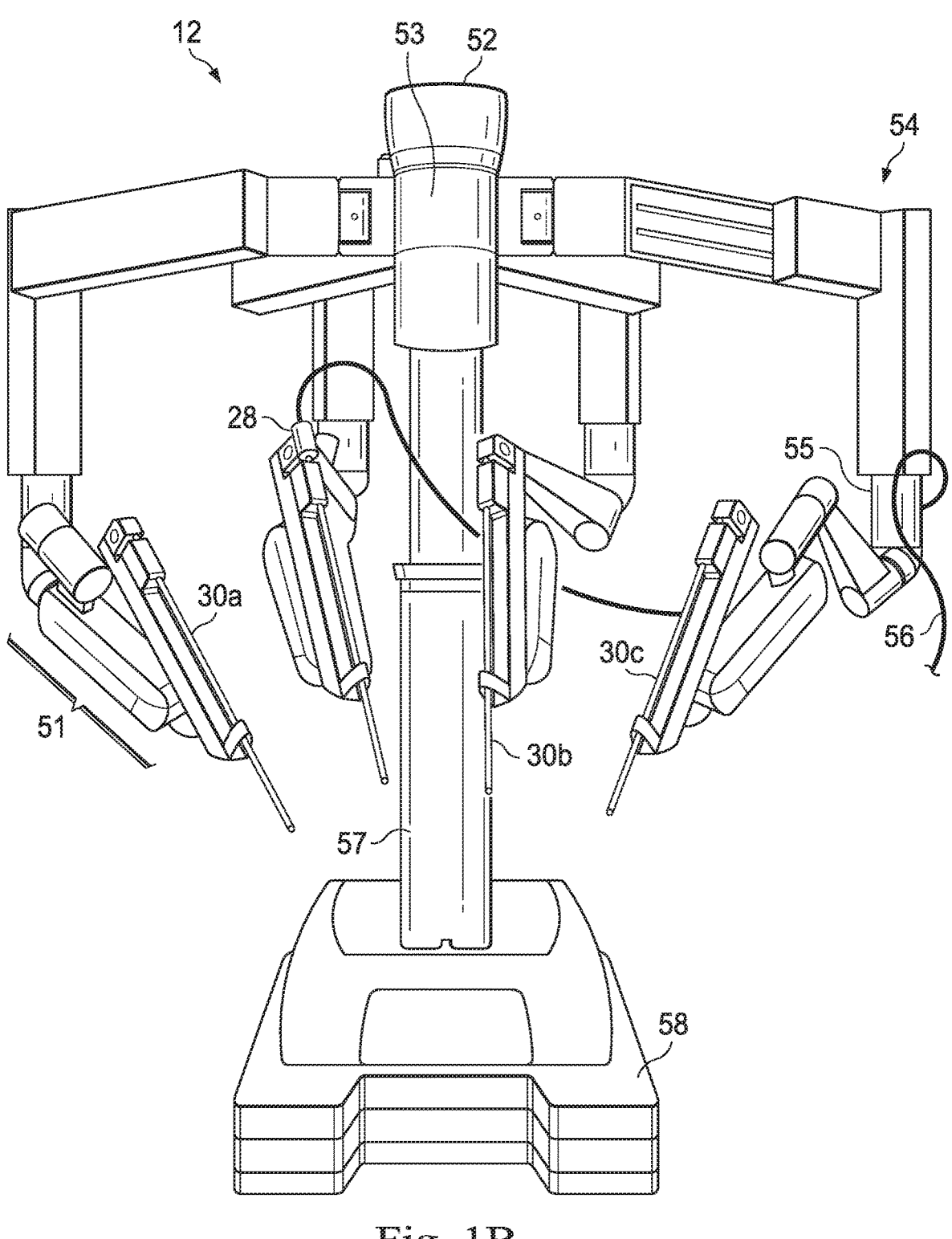
FIG. 1B is a perspective view of an assembly, in accordance with an embodiment.
Figure 1C:
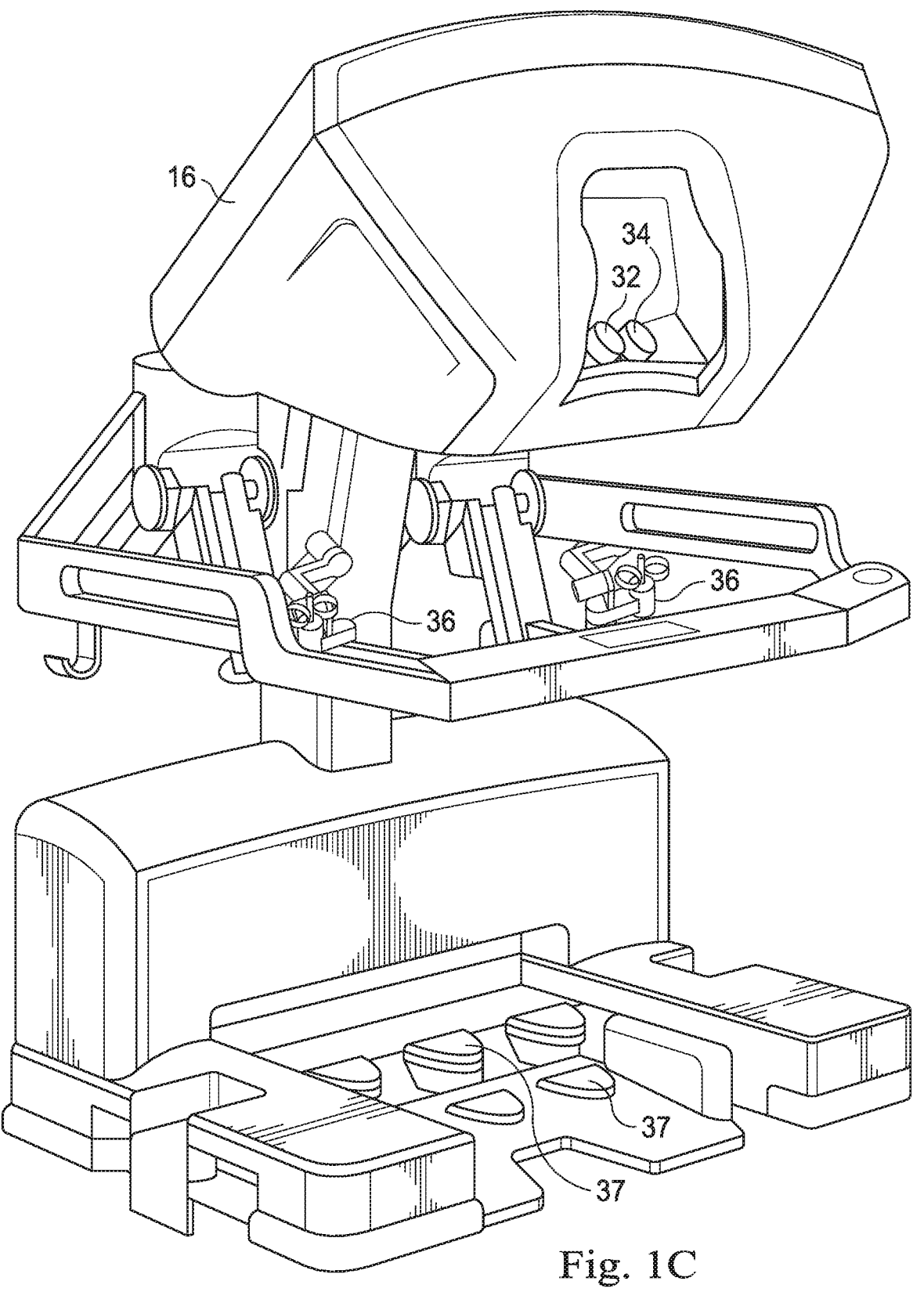
FIG. 1C is a perspective view of a surgeon's control console for a medical system, in accordance with an embodiment.

Referring now to the drawings, FIG. 1 includes FIGS. 1A, 1B, and 1C that together provide a schematic overview of a medical system 10 that may be used in, for example, medical procedures including diagnostic, therapeutic, or surgical procedures. The medical system 10 is located in a surgical environment 11. In one or more embodiments, the medical system 10 may be a teleoperational medical system that is under the teleoperational control of a surgeon. In alternative embodiments, the medical system 10 may be under the partial control of a computer programmed to perform the medical procedure or sub-procedure. In still other alternative embodiments, the medical system 10 may be a fully automated medical system that is under the full control of a computer programmed to perform the medical procedure or sub-procedure with the medical system 10. One example of the medical system 10 that may be used to implement the systems and techniques described in this disclosure is the da Vinci® Surgical System manufactured by Intuitive Surgical, Inc. of Sunnyvale, California.

As shown in FIG. 1A, the medical system 10 generally includes an assembly 12, which may be mounted to or positioned near an operating table O on which a patient P is positioned. The assembly 12 may be referred to as a patient side cart, a surgical cart, or a surgical robot. In one or more embodiments, the assembly 12 may be a teleoperational assembly. The teleoperational assembly may be referred to as, for example, a teleoperational arm cart. A medical instrument system 14 and an endoscopic imaging system 15 are operably coupled to the assembly 12. An operator input system 16 allows a surgeon or other type of clinician S to view images of or representing the surgical site and to control the operation of the medical instrument system 14 and/or the endoscopic imaging system 15.

The medical instrument system 14 may comprise one or more medical instruments. In embodiments in which the medical instrument system 14 comprises a plurality of medical instruments, the plurality of medical instruments may include multiple of the same medical instrument and/or multiple different medical instruments. Similarly, the endoscopic imaging system 15 may comprise one or more endoscopes. In the case of a plurality of endoscopes, the plurality of endoscopes may include multiple of the same endoscope and/or multiple different endoscopes.

The operator input system 16 may comprise a surgeon's console and may be located in the same room as operating table O. In some embodiments, the surgeon S and the operator input system 16 may be located in a different room or a completely different building from the patient P. The operator input system 16 generally includes one or more control device(s) for controlling the medical instrument system 14. The control device(s) may include one or more of any number of a variety of input devices, such as hand grips, joysticks, trackballs, data gloves, trigger-guns, foot pedals, hand-operated controllers, voice recognition devices, touch screens, body motion or presence sensors, and other types of input devices.

In some embodiments, the control device(s) will be provided with the same degrees of freedom as the medical instrument(s) of the medical instrument system 14 to provide the surgeon with telepresence, which is the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices that move with six degrees of freedom, and which may also include an actuatable handle for actuating instruments (for example, for closing grasping jaw end effectors, applying an electrical potential to an electrode, delivering a medicinal treatment, and actuating other types of instruments).

The assembly 12 supports and manipulates the medical instrument system 14 while the surgeon S views the surgical site through the operator input system 16. An image of the surgical site may be obtained by the endoscopic imaging system 15, which may be manipulated by the assembly 12. The assembly 12 may comprise endoscopic imaging systems 15 and may similarly comprise multiple medical instrument systems 14 as well. The number of medical instrument systems 14 used at one time will generally depend on the diagnostic or surgical procedure to be performed and on space constraints within the operating room, among other factors. The assembly 12 may include a kinematic structure of one or more non-servo controlled links (e.g., one or more links that may be manually positioned and locked in place, generally referred to as a set-up structure) and a manipulator. When the manipulator takes the form of a teleoperational manipulator, the assembly 12 is a teleoperational assembly. The assembly 12 includes a plurality of motors that drive inputs on the medical instrument system 14. In an embodiment, these motors move in response to commands from a control system (e.g., control system 20). The motors include drive systems which when coupled to the medical instrument system 14 may advance a medical instrument into a naturally or surgically created anatomical orifice. Other motorized drive systems may move the distal end of said medical instrument in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the motors may be used to actuate an articulable end effector of the medical instrument for grasping tissue in the jaws of a biopsy device or the like. Medical instruments of the medical instrument system 14 may include end effectors having a single working member such as a scalpel, a blunt blade, an optical fiber, or an electrode. Other end effectors may include, for example, forceps, graspers, scissors, or clip appliers.

The medical system 10 also includes a control system 20. The control system 20 includes at least one memory 24 and at least one processor 22 for effecting control between the medical instrument system 14, the operator input system 16, and other auxiliary systems 26 which may include, for example, imaging systems, audio systems, fluid delivery systems, display systems, illumination systems, steering control systems, irrigation systems, and/or suction systems. A clinician C may circulate within the surgical environment 11 and may access, for example, the assembly 12 during a set up procedure or view a display of the auxiliary system 26 from the patient bedside.

Though depicted as being external to the assembly 12 in FIG. 1A, the control system 20 may, in some embodiments, be contained wholly within the assembly 12. The control system 20 also includes programmed instructions (e.g., stored on a non-transitory, computer-readable medium) to implement some or all of the methods described in accordance with aspects disclosed herein. While the control system 20 is shown as a single block in the simplified schematic of FIG. 1A, the control system 20 may include two or more data processing circuits with one portion of the processing optionally being performed on or adjacent the assembly 12, another portion of the processing being performed at the operator input system 16, and the like.

Any of a wide variety of centralized or distributed data processing architectures may be employed. Similarly, the programmed instructions may be implemented as a number of separate programs or subroutines, or they may be integrated into a number of other aspects of the systems described herein, including teleoperational systems. In one embodiment, the control system 20 supports wireless communication protocols such as Bluetooth, IrDA, HomeRF, IEEE 802.11, DECT, and Wireless Telemetry.

The control system 20 is in communication with a database 27 which may store one or more clinician profiles, a list of patients and patient profiles, a list of procedures to be performed on said patients, a list of clinicians scheduled to perform said procedures, other information, or combinations thereof. A clinician profile may comprise information about a clinician, including how long the clinician has worked in the medical field, the level of education attained by the clinician, the level of experience the clinician has with the medical system 10 (or similar systems), or any combination thereof.

The database 27 may be stored in the memory 24 and may be dynamically updated. Additionally, or alternatively, the database 27 may be stored on a device such as a server or a portable storage device that is accessible by the control system 20 via an internal network (e.g., a secured network of a medical facility or a teleoperational system provider) or an external network (e.g. the Internet). The database 27 may be distributed throughout two or more locations. For example, the database 27 may be present on multiple devices which may include the devices of different entities and/or a cloud server. Additionally, or alternatively, the database 27 may be stored on a portable user-assigned device such as a computer, a mobile device, a smart phone, a laptop, an electronic badge, a tablet, a pager, and other similar user devices.

In some embodiments, control system 20 may include one or more servo controllers that receive force and/or torque feedback from the medical instrument system 14. Responsive to the feedback, the servo controllers transmit signals to the operator input system 16. The servo controller(s) may also transmit signals instructing assembly 12 to move the medical instrument system(s) 14 and/or endoscopic imaging system 15 which extend into an internal surgical site within the patient body via openings in the body. Any suitable conventional or specialized servo controller may be used. A servo controller may be separate from, or integrated with, assembly 12. In some embodiments, the servo controller and assembly 12 are provided as part of a teleoperational arm cart positioned adjacent to the patient's body.

The control system 20 can be coupled with the endoscopic imaging system 15 and can include a processor to process captured images for subsequent display, such as to a surgeon on the surgeon's console, or on another suitable display located locally and/or remotely. For example, where a stereoscopic endoscope is used, the control system 20 can process the captured images to present the surgeon with coordinated stereo images of the surgical site. Such coordination can include alignment between the opposing images and can include adjusting the stereo working distance of the stereoscopic endoscope.

In alternative embodiments, the medical system 10 may include more than one assembly 12 and/or more than one operator input system 16. The exact number of assemblies 12 will depend on the surgical procedure and the space constraints within the operating room, among other factors. The operator input systems 16 may be collocated or they may be positioned in separate locations. Multiple operator input systems 16 allow more than one operator to control one or more assemblies 12 in various combinations.

The medical system 10 may also be used to train and rehearse medical procedures. For example, the medical system 10 may be used in conjunction with the simulation system 200 described below in FIG. 2 to simulate one or more medical procedures that are to be performed on a patient.

FIG. 1B is a perspective view of one embodiment of an assembly 12 which may be referred to as a patient side cart, surgical cart, teleoperational arm cart, or surgical robot. The assembly 12 shown provides for the manipulation of three surgical tools 30a, 30b, 30c (e.g., medical instrument systems 14) and an imaging device 28 (e.g., endoscopic imaging system 15), such as a stereoscopic endoscope used for the capture of images of the site of the procedure. The imaging device may transmit signals over a cable 56 to the control system 20. Manipulation is provided by teleoperative mechanisms having a number of joints. The imaging device 28 and the surgical tools 30a-c can be positioned and manipulated through incisions in the patient so that a kinematic remote center is maintained at the incision to minimize the size of the incision. Images of the surgical site can include images of the distal ends of the surgical tools 30a-c when they are positioned within the field-of-view of the imaging device 28.

The assembly 12 includes a drivable base 58. The drivable base 58 is connected to a telescoping column 57, which allows for adjustment of the height of arms 54. The arms 54 may include a rotating joint 55 that both rotates and moves up and down. Each of the arms 54 may be connected to an orienting platform 53. The arms 54 may be labeled to facilitate trouble shooting. For example, each of the arms 54 may be emblazoned with a different number, letter, symbol, other identifier, or combinations thereof. In FIG. 1B, the arms 54 are numbered from one to four. The orienting platform 53 may be capable of 360 degrees of rotation. The assembly 12 may also include a telescoping horizontal cantilever 52 for moving the orienting platform 53 in a horizontal direction.

In the present example, each of the arms 54 connects to a manipulator arm 51. The manipulator arms 51 may connect directly to a medical instrument, e.g., one of the surgical tools 30a-c. The manipulator arms 51 may be teleoperatable. In some examples, the arms 54 connecting to the orienting platform 53 may not be teleoperatable. Rather, such arms 54 may be positioned as desired before the surgeon S begins operation with the teleoperative components. Throughout a surgical procedure, medical instruments may be removed and replaced with other instruments such that instrument to arm associations may change during the procedure.

Endoscopic imaging systems (e.g., endoscopic imaging system 15 and imaging device 28) may be provided in a variety of configurations including rigid or flexible endoscopes. Rigid endoscopes include a rigid tube housing a relay lens system for transmitting an image from a distal end to a proximal end of the endoscope. Flexible endoscopes transmit images using one or more flexible optical fibers. Digital image-based endoscopes have a "chip on the tip" design in which a distal digital sensor such as a one or more charge-coupled device (CCD) or a complementary metal oxide semiconductor (CMOS) device store image data. Endoscopic imaging systems may provide two- or three-dimensional images to the viewer. Two-dimensional images may provide limited depth perception. Three-dimensional stereo endoscopic images may provide the viewer with more accurate depth perception. Stereo endoscopic instruments employ stereo cameras to capture stereo images of the patient anatomy. An endoscopic instrument may be a fully sterilizable assembly with the endoscope cable, handle and shaft all rigidly coupled and hermetically sealed.

FIG. 1C is a perspective view of an embodiment of the operator input system 16, which may be referred to as a surgeon's console. The operator input system 16 includes a left eye display 32 and a right eye display 34 for presenting the surgeon S with a coordinated stereo view of the surgical environment that enables depth perception. The operator input system 16 further includes one or more input control devices 36, which in turn cause the assembly 12 to manipulate one or more instruments of the endoscopic imaging system 15 and/or medical instrument system 14. The input control devices 36 can provide the same degrees of freedom as their associated instruments to provide the surgeon S with telepresence, or the perception that the input control devices 36 are integral with said instruments so that the surgeon has a strong sense of directly controlling the instruments. To this end, position, force, and tactile feedback sensors (not shown) may be employed to transmit position, force, and tactile sensations from the medical instruments, e.g., surgical tools 30a-c, or imaging device 28, back to the surgeon's hands through the input control devices 36. Input control devices 37 are foot pedals that receive input from a user's foot. Aspects of the operator input system 16, the assembly 12, and the auxiliary systems 26 may be adjustable and customizable to meet the physical needs, skill level, or preferences of the surgeon S.

Figure 2:
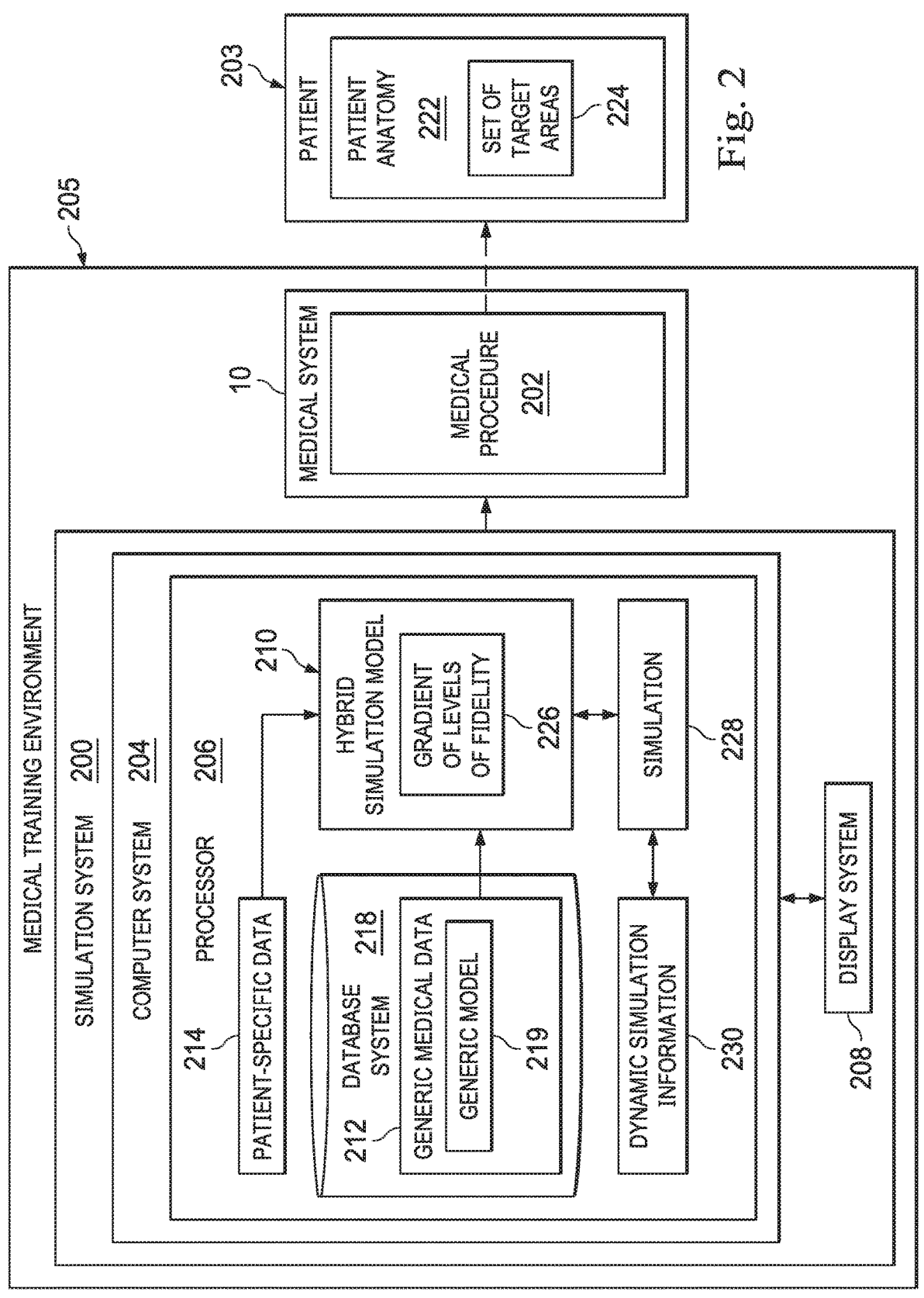
FIG. 2 is a block diagram of a simulation system that is used to simulate a medical procedure that is to be performed on a patient, in accordance with an embodiment.

FIG. 2 is a block diagram of a simulation system 200 that is used to simulate a medical procedure 202 that is to be performed on a patient 203 (e.g. the patient P) in a medical training environment 205. In one or more embodiments, the medical procedure 202 is to be performed in a surgical environment (e.g. the surgical environment 11 in FIG. 1A).

The simulation system 200 includes a computer system 204. The computer system 204 may include a single computer or multiple computers in communication with each other. The computer system 204 may include at least one processor 206. The processor 206 may be used to run executable code stored on memory to simulate the medical procedure 202. In one embodiment, the simulation system 200 is separate from the control system 20 described in FIG. 1. In other embodiments, the simulation system 200 may be implemented as part of the control system 20. In still other embodiments, the processor 206 of the simulation system 200 may be implemented using the processor 22 of the control system 20 in FIG. 1.

In one or more embodiments, the simulation system 200 also includes a display system 208 coupled to the processor 206. In other embodiments, the display system 208 may be considered separate from the simulation system 200. The display system 208 may include one or more display devices communicatively coupled to the processor 206. In one or more embodiments, the display system 208 may be coupled to the surgeon's console of the operator input system 16.

The simulation system 200 creates a hybrid simulation model 210 that integrates generic medical data 212 (e.g. for a representative patient) with patient-specific data 214 for the patient 203, and then dynamically modifies the hybrid simulation model 210 based on information or parameters that change during a simulation (i.e. a virtual reality simulation) of the medical procedure 202. This process of generating the hybrid simulation model 210 reduces the overall time, effort, and processing resources that are needed to generate a simulation model.

The simulation system 200 may retrieve the generic medical data 212 from a database system 218. The database system 218 may include one or more databases. The generic medical data 212 includes information that is not specific to the particular patient 203. For example, the generic medical data 212 may include general information about the medical procedure 202 and/or information about a representative patient or a representative group of patients. In one or more embodiments, the generic medical data 212 includes a generic model 219 of a representative patient or a representative group of patients. Examples of different types of generic medical data 212 that may be retrieved from the database system 218 are described in FIG. 3 below. In one or more embodiments, the simulation system 200 receives patient-specific data 214 that includes information specific to the particular patient 203. Examples of different types of patient-specific data 214 are described in FIG. 4 below.

The simulation system 200 integrates the generic medical data 212 and the patient-specific data 214 to generate the hybrid simulation model 210 that is customized for the patient 203. In one or more embodiments, the simulation system 200 uses the patient-specific data 214 to modify, enhance, or otherwise refine the generic medical data 212 for regions of interest in the patient anatomy 222 of the patient 203. As one example, the patient-specific data 214 may be used to scale and/or morph the generic model 219. Further, portions of the generic model 219 representing, adjacent to, and/or related a set of target areas 224 towards which the medical procedure 202 is directed may be modified using the patient-specific data 214.

The set of target areas 224 may include, for example, one or more diseased anatomical structures of the patient anatomy 222 of the patient 203. An anatomical structure may include, for example, one or more of an organ, an organ system, a muscle, a nerve, an artery, a vein, a bone, a bone structure, a ligament, some other type of anatomical structure or tissue, or a combination thereof. By only modifying the portions of the generic model 219 that represent, are adjacent to, and/or are related to the set of target areas 224, the simulation system 200 reduces the overall time, effort, and processing resources needed to generate a hybrid simulation model 210 that is customized for the patient 203.

In one or more embodiments, because of the integration of the generic medical data 212 with the patient-specific data 214, the hybrid simulation model 210 represents the patient anatomy 222 of the patient 203 with varying levels of fidelity. For example, each anatomical structure of the patient anatomy 222 is represented in the hybrid simulation model 210 with a particular level of fidelity. The level of fidelity indicates how accurately the modeled anatomical structure in the hybrid simulation model 210 matches the actual geometry and properties of the corresponding actual anatomical structure of the patient 203.

In some embodiments, the hybrid simulation model 210 represents the patient anatomy 222 of the patient 203 with a gradient of levels of fidelity 226. For example, the level of fidelity of modeled anatomical structures may decrease as the distance from an operational path of the medical procedure 202 increases. The operational path may be, for example, a surgical path for performing the medical procedure 202, a procedural path, or some other path (external and/or internal) relative to the patient anatomy 222. When the medical system 10 described in FIG. 1 is to be used to perform the medical procedure 202, the surgical path may include, for example, the path relative to the patient anatomy 222 of the patient 203 that is to be followed by each of the arms 54 and each of the surgical instruments and tools that make up the medical instrument system 14 of the assembly 12 described in FIGS. 1A and 1B during the medical procedure 202.

For example, the representation of the set of target areas 224 in the hybrid simulation model 210 may have a level of fidelity that is higher than the level(s) of fidelity of portions of the hybrid simulation model 210 that represent anatomical structures that will not be affected by or interacted with during the medical procedure 202. If the medical procedure 202 is a cardiologic surgical procedure, the set of target areas 224 may include the heart of the patient 203 as well as areas surrounding the heart. However, the heart surgical procedure would likely never involve the limbs of the patient 203. Accordingly, the limbs may be represented in the hybrid simulation model 210 with a lower level of fidelity than the heart or even other anatomical structures within the chest cavity of the patient 203. In some cases, the anatomical structures of the abdomen of the patient 203 would be represented with a higher level of fidelity than the limbs but a lower level of fidelity compared to the heart.

The resulting hybrid simulation model 210 generated by the simulation system 200 may be used to run highly customized, high-quality simulations of the medical procedure 202 to be performed on the patient 203. For example, the simulation system 200 may perform a simulation 228 of the medical procedure 202 using the hybrid simulation model 210 and dynamic simulation information 230 that corresponds to at least one of the medical procedure 202 or the patient 203. The simulation 228 may be a dynamic simulation. The dynamic simulation information 230 may include information about how the patient 203 and/or the patient anatomy 222 would be affected by the medical procedure 202, as well as other information about the medical procedure 202 that does not remain static during the simulation of the medical procedure 202. Examples of the dynamic simulation information 230 are described in FIG. 5 below.

The simulation 228 may be rendered on the display system 208 such that a surgeon, a member of the surgical team, or other medical personnel may use simulation 228 to rehearse the medical procedure 202. Because the simulation 228 of the medical procedure 202 is performed using the hybrid simulation model 210 and the dynamic simulation information 230, the simulation 228 provides a much higher level of overall fidelity in representing how the medical procedure 202 will proceed for a particular patient 203 as compared to a simulation run using the generic model 219 for the patient 203.

The simulation 228 may be performed in, for example, environment 11 in FIG. 1A to rehearse or otherwise train for the medical procedure 202. In one or more embodiments, the simulation 228 may be performed using, for example, medical system 10 in FIG. 1. For example, the simulation 228 may be performed using operator input system 16, assembly 12, or both. The operator input system 16 may include a single surgeon's console or a dual surgeon's console.

As the simulation 228 is run, the simulation 228 uses the dynamic simulation information 230 to account for the effects of simulated interactions between the anatomical structure of the patient anatomy 222 and the instruments that are used to perform the medical procedure 202. Thus, the simulation system 200 dynamically scales or morphs the hybrid simulation model 210 using the dynamic simulation information 230 such that the simulation 228 provides an experience more similar to what the actual medical procedure 202 will be like. This type of simulation 228 allows a surgeon or other medical personnel to rehearse the medical procedure 202 with a greater level of realism. However, because the hybrid simulation model 210 is generated beginning with generic medical data 212 that is customized using the patient-specific data 214, the overall time, effort, and processing resources spent in generating the hybrid simulation model 210 are reduced as compared to generating a model that captures the entire patient anatomy 222 of the patient 203 with the highest level of fidelity.

Figure 3:
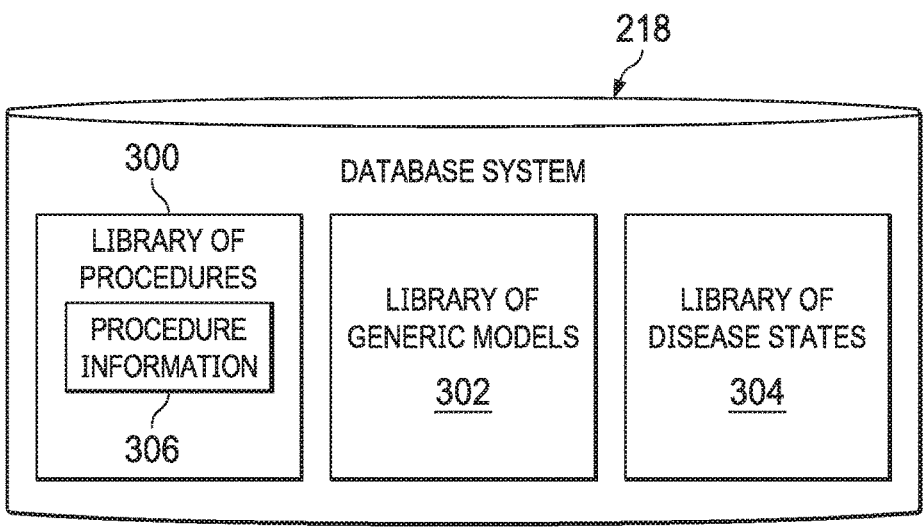
FIG. 3 is a block diagram illustrating the different types of generic data that may be found in a database system, in accordance with an embodiment.

FIG. 3 is a block diagram illustrating the different types of generic medical data 212 that may be found in the database system 218. The database system 218 may include, for example, a library of procedures 300, a library of generic models 302, and a library of disease states 304. Each of these three libraries may be implemented using one or more databases or other types of data repositories.

The library of procedures 300 may store information related to one or more medical procedures, including the medical procedure 202 to be performed on the patient 203 described in FIG. 2. In one example embodiment, the library of procedures 300 stores procedure information 306 for the medical procedure 202. The procedure information 306 identifies the various stages and/or steps of the medical procedure 202. The procedure information 306 may identify, for example, but is not limited to, the anatomical structures that are known to be adjacent to the one or more diseased anatomical structures to be surgically addressed by the medical procedure 202, the surgical path to be followed by the medical instruments when performing the medical procedure 202, the critical anatomical landmarks at which intraoperative decisions are to be made, a length or range of time that is expected to be spent at various anatomical structures along the surgical path during the medical procedure, and other types of information about the medical procedure 202.

The library of generic models 302 stores one or more generic models representing the anatomy of representative patients. In one or more embodiments, the library of generic models 302 stores a first generic model for a first representative group of patients and a second generic model for a second representative group of patients. The first representative group of patients may be healthy females, while the second representative group of patients may be healthy males. In other embodiments, the library of generic models 302 stores a first plurality of generic models for the first representative group of patients and a second plurality of generic models for the second representative group of patients. The first plurality of generic models may include generic models that are scaled to common female anthropometries, while the second plurality of generic models may include generic models that are scaled to common male anthropometries. For example, the first plurality of generic models may include one generic model for a certain height and weight class of healthy females, another generic model for another height and weight class of healthy females, and yet another generic model for yet another height and weight class of healthy females.

Thus, the library of generic models 302 stores generic, simulation-ready models that may be retrieved by the simulation system in FIG. for use in generating the hybrid simulation model 210. Any one of the generic models stored in the library of generic models 302 may be retrieved by the simulation system 200 and used as the generic model 219 that is later modified using the patient-specific data 214 as described in FIG. 2.

In one or more embodiments, the library of disease states 304 stores information about the properties of any number of anatomical structures when afflicted by various types of disease states. For example, the library of disease states 304 may store information about the material properties of a heart afflicted by one type of disease as well as information about the material properties of a heart afflicted by another type of disease.

Figure 4:
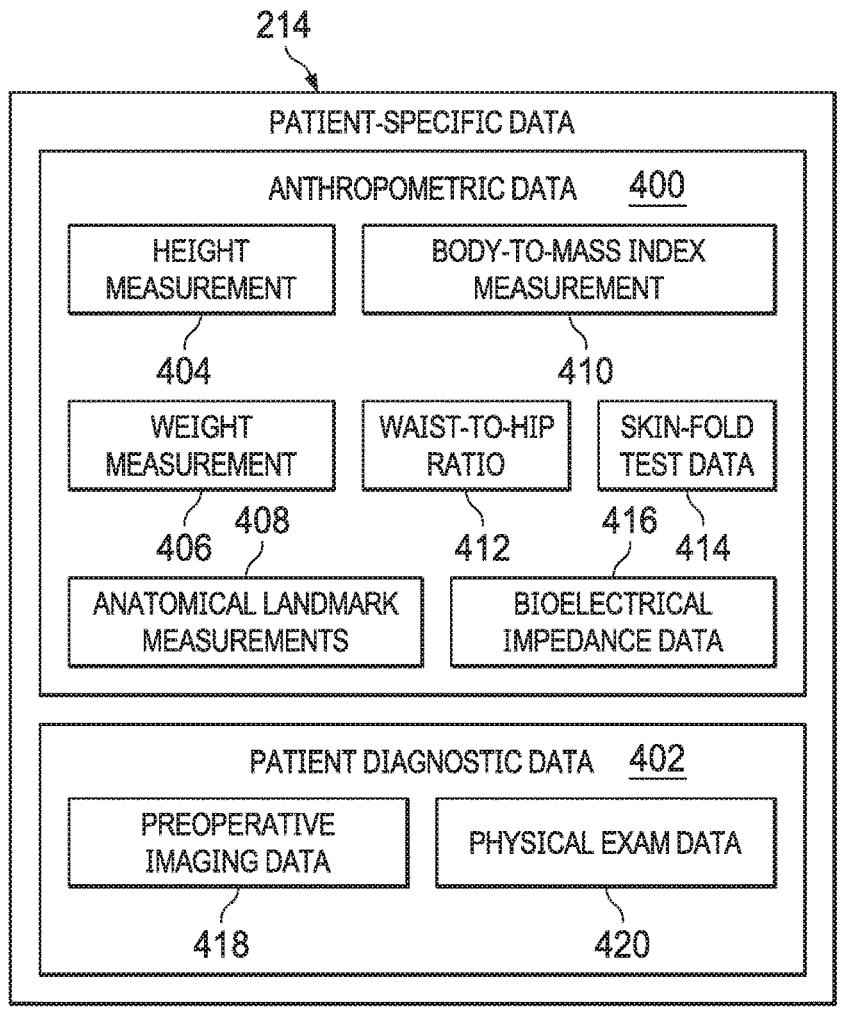
FIG. 4 is a block diagram illustrating the different types of patient-specific data that may be found in a database system, in accordance with an embodiment.

FIG. 4 is a block diagram illustrating different types of patient-specific data 214. The patient-specific data 214 may include, for example, anthropometric data 400 and patient diagnostic data 402 that are specific to the patient 203 described in FIG. 2. The anthropometric data 400 for the patient 203 includes data, or measurements, that are used to assess the size, shape, and composition of the patient 203. The anthropometric data 400 may include, for example, but is not limited to, a height measurement 404, a weight measurement 406, anatomical landmark measurements 408, a body-to-mass index (BMI) measurement 410, a waist-to-hip ratio 412, skin-fold test data 414, bioelectrical impedance data 416, some other type of anthropometric measurement, or a combination thereof. The anatomical landmark measurements 408 may include, for example, measurements of the distance between key bones or other anatomic landmarks of the patient anatomy 222 of the patient 203. The simulation system 200 in FIG. 2 may use the anthropometric data 400 to generate scaling factors that can be applied to a generic model of a representative patient retrieved from the library of generic models 302 in FIG. 3 to thereby customize the generic model for the patient 203.

The patient diagnostic data 402 includes information about specific anatomical structures of the patient 203. In one or more embodiments, the patient diagnostic information includes information about the geometry of the set of target areas 224 in FIG. 2 towards which the medical procedure 202 is directed as well as information about the geometry of one or more anatomical structures adjacent to or functionally related to each of the set of target areas 224. For example, the patient diagnostic data 402 may include preoperative imaging data 418, physical exam data 420, and/or other types of diagnostic information that provides information about the set of target areas 224 and, in some cases, anatomical structures adjacent to or functionally related to each of the set of target areas 224. The preoperative imaging data 418 may include, for example, but is not limited to, ultrasound images, x-ray images, medical resonance imaging (MRI) images, computed tomography (CT) images, or other types of imaging data. The physical exam data 420 may include information about the patient anatomy 222 that can be gleaned from, for example, observation, palpation, percussion, and auscultation of the patient 203. The simulation system 200 in FIG. 2 may use the patient diagnostic data 402 to modify the geometry of and/or other types of properties of the anatomical structures in a generic model of a representative patient, which may be retrieved from the library of generic models 302 in FIG. 3, to thereby customize the generic model for the patient 203.

Figure 5:
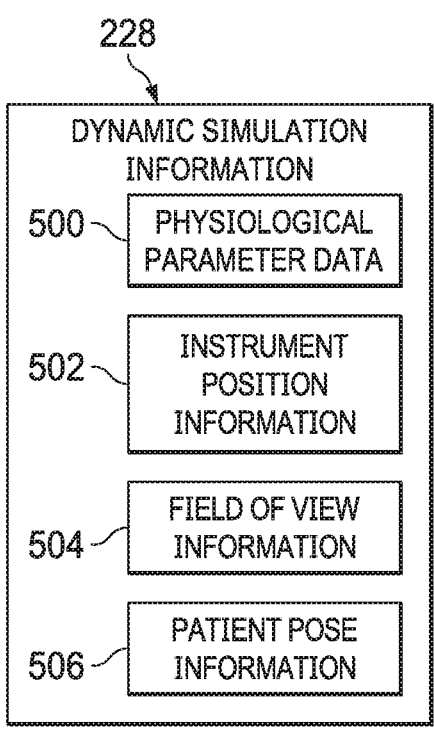
FIG. 5 is a block diagram illustrating different types of dynamic simulation information, in accordance with an embodiment.

FIG. 5 is a block diagram illustrating different types of dynamic simulation information 230. The dynamic simulation information 230 includes information about one or more parameters that are expected to change during the simulation 220 of the medical procedure 202 run using the hybrid simulation model 210. For example, the dynamic simulation information 230 may include physiological parameter data 500, instrument position information 502, field of view information 504, patient pose information 506, as well as other types of information. In one or more embodiment, the simulation system 200 of FIG. 2 uses the instrument position information 502, the field of view information 504, and the patient pose information 506 during the simulation 228 to dynamically adjust the rendering or presentation of the hybrid simulation model 210 during the simulation 228 to improve the accuracy and realism of the simulation 228.

The physiological parameter data 500 includes data for a plurality of physiological parameters that may change, or are expected to change, during the medical procedure 202. In particular, the physiological parameter data 500 includes information about how anatomical structures within the patient 203 should look and respond to the simulated interactions between these anatomical structures and the instruments and/or agents used to perform the medical procedure 202. For example, during the simulation 228 of the medical procedure 202, the simulated effects of suction, irrigation, impedance cardiography, as well as other steps or procedures performed as part of the medical procedure 202 may result in simulated changes in the plurality of physiological parameters. The plurality of physiological parameters may include, for example, without limitation, arterial and venous pressure, respiration rate, insufflation pressure, tissue response to energy application, tissue response to physical contact with one or more instruments, and/or other types of physiological parameters. The simulation system 200 of FIG. 2 may use the physiological parameter data 500 to ensure that the simulation 228 of the medical procedure 202 accounts for simulated changes in the physiological parameters. For example, the simulation system 200 may use the physiological parameter data 500 to dynamically adjust the rendering of the hybrid simulation model 210 on the display system 208 during the simulation 228 in a manner that accounts for the simulated changes in the physiological parameters. More specifically, the simulation system 200 may adjust the visualization of the hybrid simulation model 210 to account for these simulated changes.

The instrument position information 502 includes information about how the positions of the instruments (e.g. instruments of the medical instrument system 14 in FIG. 1, a retractor, an endoscope, a scalpel, a suction tube, an irrigation tube, a laser device, a grasping tool, etc.) may change, or are expected to change, over the course of the medical procedure 202. As one example, the instrument position information 502 may include information about how the position of an endoscope (e.g. the endoscopic imaging system 15 in FIG. 1) is expected to move or change during the medical procedure 202. The simulation system 200 may use the instrument position information 502 to dynamically adjust the rendering of the hybrid simulation model 210 on the display system 208 during the simulation 228 in a manner that accounts for these changes in the position of the endoscope.

Similarly, the simulation system 200 may use the field of view information 504 to dynamically adjust the rendering of the hybrid simulation model 210 on the display system 208 during the simulation 228 in a manner that accounts for changes in one or more fields of view or perspectives. The field of view information 504 includes information about one or more different fields of view. For example, the field of view information 504 may include instrument-based field of view information, vision-based field of view information, some other type of field of view or perspective information, or a combination thereof.

Instrument-based field of view information may include, for example, information about what anatomical structures a surgeon or other medical personnel may actually see in the field of view of one or more imaging instruments, such as an endoscope, a camera, etc. For example, the field of view information 504 may include information about the position of the imaging instrument and a calculation of the field of view of the imaging instrument as the imaging instrument moves during the simulation of the medical procedure 202. Vision-based field of view information includes information from the perspective of a surgeon or other clinician. For example, the field of view information may be from the perspective of what would be visible to a surgeon or other clinician during the medical procedure 202.

The patient pose information 506 includes information about how the position and/or orientation of the patient 203 may change during the medical procedure 202. In some embodiments, the position and/or orientation of the patient 203 is determined by the position and/or orientation of the bed, operating table, or other type of structure on which the patient 203 is positioned during the medical procedure 202. The patient pose information 506 may include information about how gravity affects the patient 203 based on the position and/or orientation of the patient 203. For example, the patient pose information 506 may include information about the position and/or orientation of the patient 203 might cause one or more anatomical structures to deform during the medical procedure 202. The simulation system 200 may use the patient pose information 506 to dynamically adjust the rendering of the hybrid simulation model 210 on the display system 208 during the simulation 228 in a manner that accounts for these changes in the pose of the patient 203.

Figure 6:
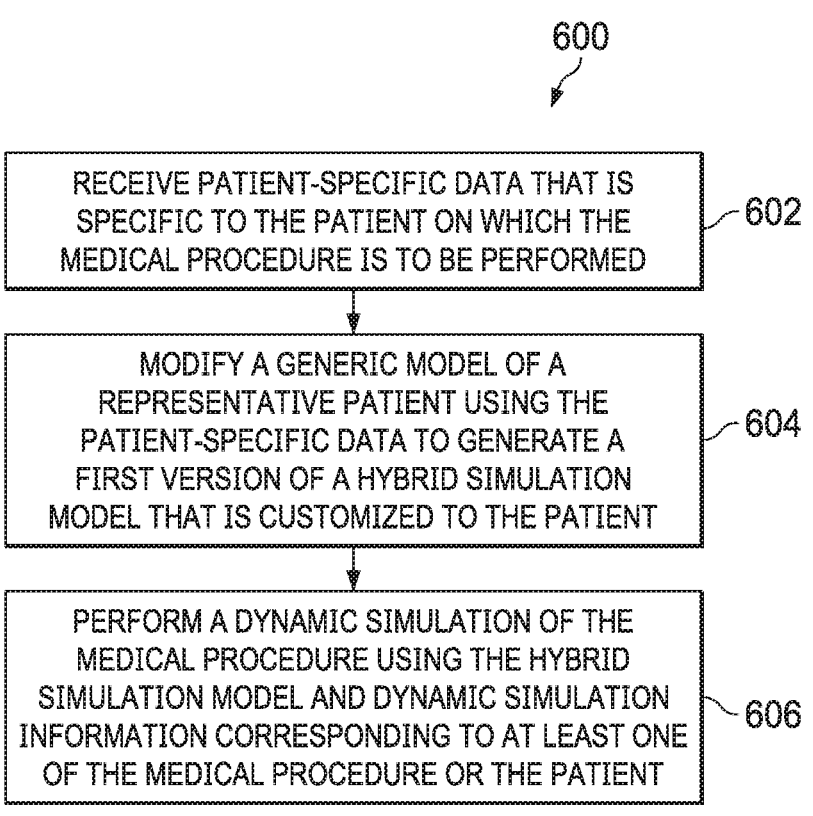
FIG. 6 is a flowchart illustration of a method for simulating medical procedure that is to be performed on a patient, in accordance with an embodiment.

FIG. 6 is a flowchart illustration of a method 600 for simulating medical procedure that is to be performed on a patient. In one or more embodiments, the medical procedure is to be performed in a surgical environment, such as the surgical environment 11 of FIG. 1. The method 600 is illustrated in FIG. 6 as a set of operations or processes 602 through 608 and is described with continuing reference to FIGS. 2-5. Not all of the illustrated processes 602 through 608 may be performed in all embodiments of method 600. Additionally, one or more processes that are not expressly illustrated in FIG. 6 may be included before, after, in between, or as part of the processes 602 through 608. In some embodiments, one or more of the processes 602 through 608 may be implemented, at least in part, in the form of executable code stored on non-transitory, tangible, machine-readable media that when run by one or more processors (e.g., the processors of control system) may cause the one or more processors to perform one or more of the processes.

At process 602, patient-specific data 214 that is specific to the patient 203 on whom the medical procedure 202 is to be performed is received. The patient-specific data 214 may include, for example, anthropometric data 400, patient diagnostic data 402, or a combination of the two.

At process 604, a generic model 219 of a representative patient is modified using the patient-specific data 214 to generate a hybrid simulation model 210 that is customized to the patient 203. The generic model 219 may be retrieved from the database system 218. In particular, in one embodiment, the generic model 219 may be retrieved from the library of generic models 302. The generic model 219 may be a model of the anatomy of a healthy female or male, depending on the gender of the patient 203. In one or more embodiments, the generic model 219 selected for use may represent the anatomy of a healthy female or male having anthropometric measurements common to or within a selected range of the patient 203.

In one or more embodiments, modifying the generic model 219 includes modifying a representation of each of a plurality of anatomical structures in the generic model 219 along operating path along which the medical procedure 202 is to be performed based on the patient-specific data 214 received to thereby generate the hybrid simulation model 210. In some embodiments, the modification of the generic model 219 using the patient-specific data 214 in process 604 includes scaling and/or morphing the generic model 219 based on the anthropometric data 400. Further, the modification may include adjusting one or more portions of the generic model 219 based on the patient diagnostic data 402. For example, if preoperative imaging data 418 indicates that the patient 203 has an enlarged liver and the medical procedure 202 to be performed involves performing a biopsy of this liver, the generic model 219 may be modified such that the representation of the liver in the generic model 219 is enlarged accordingly. In this manner, this portion of the generic model 219 is customized to the patient 203. Thus, the generic model 219 may be customized based on a set of target areas 224 towards which the medical procedure 202 is directed.

At process 606, a simulation 228 of the medical procedure 202 is performed using the hybrid simulation model 210 and dynamic simulation information 230 corresponding to at least one of the medical procedure 202 or the patient 203. In one or more embodiments, performing the simulation 228 includes running the simulation 228 using the hybrid simulation model 210 and simulated (or computerized) versions of the instruments that are to interact with the patient 203 during the medical procedure 202. In other embodiments, performing the simulation 228 may include a surgeon, a member of the surgical team, or other medical personnel using the medical system 10 described in FIG. 1 to interact with the hybrid simulation model 210 and thereby train for or rehearse the medical procedure 202.

During the simulation 228 in process 606, dynamic simulation information 230 is used to render a first portion of the hybrid simulation model 210 representing a patient anatomy 222 of the patient 203 that interacts with the medical procedure 202 at a level of fidelity that is higher than a level of fidelity at which a second portion of the hybrid simulation model 210 representing the patient anatomy 222 that does not interact with the medical procedure 202 at any step of the medical procedure 202. In one or more embodiments, performing the simulation 228 includes simulating, dynamically, the medical procedure 202 using the hybrid simulation model 210 and the dynamic simulation information 230 such that the patient anatomy 222 of the patient 203 is represented with a gradient of levels of fidelity 226. For example, a level of fidelity of anatomical structures in the hybrid simulation model 210 may decrease during the simulation as a distance from a surgical path of the medical procedure 202 increases.

Performing the simulation 228 may include using patient pose information 506 to adjust how one or more anatomical structure of the patient anatomy 222 in the hybrid simulation model 210 deform in response to expected changes to a pose of the patient 203 during the simulation 228. Performing the simulation 228 may also include adjusting a visualization of the hybrid simulation model 210 during the simulation 228 to account for effects of simulated interactions between anatomical structures and instruments based on the dynamic simulation information 230. These instruments may include any number of manually-controlled instruments, robotically-controlled instruments, or both.

For example, the simulation system 200 may take into account how changes in the position of one or more instruments during the medical procedure 202 may affect the portions of the patient anatomy 222 in the hybrid simulation model 210 along the surgical path. The simulation system 200 may use this instrument position information 502 to adjust the rendering of the hybrid simulation model 210 on the display system 208 to aid a surgeon or clinician who is rehearsing the medical procedure 202. The simulation system 200 may also use field of view information 504 to adjust the rendering of the hybrid simulation model 210. In some embodiments, the simulation system 200 may actually modify or recreate one or more portions of the hybrid simulation model 210 based on the position of the instruments.

Thus, the simulation 228 using the hybrid simulation model 210 is customized to both the patient 203 and the medical procedure 202 to be performed on the patient 203. The simulation 228 dynamically adapts the hybrid simulation model 210 to each step or stage of the medical procedure 202 such that a portion of the patient anatomy 222 that interacts with the medical procedure 202 at each step is rendered at a higher level of fidelity than other portions of the patient anatomy 222. This type of simulation 228 provides representation of the medical procedure 202 to be performed on the patient 203 having a desired level of accuracy.

FIG. 7 is a flowchart illustration of a method 700 for generating a hybrid simulation model for use in simulating a medical procedure that is to be performed on a patient. In one or more embodiments, the medical procedure is to be performed in a surgical environment, such as the surgical environment 11 of FIG. 1. The method 700 is illustrated in FIG. 7 as a set of operations or processes 702 through 716 and is described with continuing reference to FIGS. 2-5.

Further, the method 700 illustrated in FIG. 7 may be a more detailed method for generating a hybrid simulation model than the method 600 described in FIG. 6 above. Not all of the illustrated processes 702 through 716 may be performed in all embodiments of method 700. Additionally, one or more processes that are not expressly illustrated in FIG. 7 may be included before, after, in between, or as part of the processes 702 through 716. In some embodiments, one or more of the processes 702 through 716 may be implemented, at least in part, in the form of executable code stored on non-transitory, tangible, machine-readable media that when run by one or more processors (e.g., the processors of control system) may cause the one or more processors to perform one or more of the processes.

At process 702, anthropometric data 400 and patient diagnostic data 402 are received at the simulation system 200. At process 704, a generic model 219 of a representative patient is selected based on the anthropometric data 400 received. For example, a generic model 219 of a representative patient of the same gender and of a same height and weight class as the patient 203 may be selected. At process 706, the generic model 219 is scaled and/or morphed based on the anthropometric data 400. This scaling and/or morphing may be a further refinement of the generic model 219 based on the precise height and weight of the patient 203, the body-to-mass index of the patient 203, and/or other measurements of the patient 203.

At process 708, a surgical path and a plurality of anatomical structures along the surgical path are identified based on procedure information 306 about the medical procedure 202 to be performed on the patient 203. At process 710, the representation of each of the plurality of anatomical structures along the surgical path is modified based on the patient diagnostic data 402 received to thereby finalize a hybrid simulation model 210. Thus, the hybrid simulation model 210 is generated by combining generic information with relevant patient-specific information.

At process 712, the simulation 228 of the medical procedure 202 to be performed on the patient 203 is run using the hybrid simulation model 210 and dynamic simulation information 230. For example, a surgeon may use the medical system 10 described in FIG. 1 to simulate performing the medical procedure 202 with the hybrid simulation model 210. During the simulation 228, the simulation system 200 uses the dynamic simulation information 230 to adjust the visualization or rendering of the hybrid simulation model 210 on the display system 208 to account for effects of simulated interactions between anatomical structures of the patient 203 and instruments and/or agents used in the medical procedure 202. The simulation 228 dynamically adapts to each step of the medical procedure 202 such that a portion of a patient anatomy 222 of the patient 203 that interacts with the medical procedure 202 at each step of the medical procedure 202 is rendered at a higher level of fidelity.

In one or more example embodiments, the hybrid simulation model 210 may be "smart" about what is rendered in higher fidelity during the simulation 228 of the medical procedure 202. For example, higher-fidelity rendering may be applied on the fly, as needed, to anatomical structures that are dynamically interacting with the instruments, endoscope, other agents (e.g. suction, irrigation, etc.), and/or gravity during the simulation of the medical procedure 202. With this type of approach, a diseased anatomical structure (e.g. prostate) may not need to be rendered in high fidelity, while the surgeon is performing initial dissection steps (e.g. dropping the bladder).

In other embodiments, the hybrid simulation model 210 may allow the simulation 228 to begin with a lower fidelity rendering. As the simulation 228 progresses, the rendering of the corresponding portions of the hybrid simulation model 210 would "snap" to the appropriate level of fidelity based on the step or stage of the medical procedure 202 that is being simulated. In some embodiments, the hybrid simulation model 210 would be able to provide a desired level of fidelity for any relevant anatomical structure whenever an instrument, agent, or gravity interacts with the anatomical structure during the simulation 228 of the medical procedure.

At process 714, simulation data is computed based on the simulation 228 of the medical procedure 202. The simulation data, which may be feedback data, may be computed during the simulation 228, after the simulation 228 has been completed, or both. The simulation data may include information about the simulation 228 itself as well as patient-specific intraoperative data. For example, the simulation data may include data about how the simulation 228 of the medical procedure 202 compares to the expected performance and outcome of the medical procedure 202. For example, the simulation data may include data about the efficiency of the simulation 228, a measurement of the success of the simulation 228, data about the time spent at each step of the medical procedure 202, data about the simulated interactions between the medical system 10 and the patient anatomy 222, data about the simulated effects of changes in patient pose on the patient anatomy 222 during the simulation 228 as compared to the patient pose information 506, other types of data, or a combination thereof.

In some embodiments, the simulation data includes information that may be used for preoperative planning. As one example, the simulation data may be used to improve medical instrument selection, improve medical instrument calibration, improve patient preparation before the medical procedure 202, or a combination thereof, to thereby increase procedural or operational efficiency of the medical procedure 202.

At process 716, the hybrid simulation model 210 is modified using the simulation data computed to form an updated hybrid simulation model 210. The updated hybrid simulation model 210 may allow a second simulation 228 to be run with even higher fidelity than the first simulation 228. In some embodiments, at process 716, the hybrid simulation model 210 is modified based on user input. At process 718, the dynamic simulation information 230 is modified based on the simulation data computed to form updated dynamic simulation information 230. This updated dynamic simulation information 230 takes into account the results of the simulation 228 to provide updated information that can be used for dynamically adjusting another simulation of the medical procedure 202. In some embodiments, at process 718, the dynamic simulation information 230 is modified based on user input.

At process 720, a new simulation of the medical procedure 202 is performed using the updated hybrid simulation model 210 and the updated dynamic simulation information 230. Performing the new simulation using the updated hybrid simulation model 210 and the updated dynamic simulation information 230 may provide an even finer level of customization to both the patient 203 and the medical procedure 202.

In some embodiments, processes 714 through 720 may be repeated multiple times to further refine and customize the hybrid simulation model 210. Processes 714 through 720 may be repeated any number of times until a desired version of the hybrid simulation model 210 with the desired level of refinement and overall fidelity and customization has been generated. The simulation data generated over the multiple runs of the simulation 228 may be used as patient-specific intraoperative guidance data. For example, this simulation data may be used to generate instructions for controlling the medical system 10 to actually perform the medical procedure 202 on the patient 203.

In some embodiments, the simulation data may be fed into a learning algorithm or learning program for use in providing information about how to improve the medical procedure 202. The simulation data may provide useful information about actions that, if performed during the medical procedure 202, would result in less than desirable outcomes. In one or more embodiments, the simulation data may be used to identify the optimal set and/or sequence of actions to be performed during the medical procedure 202 to allow for the best possible outcome. In some embodiments, the simulation data may be used to help train other surgeons or clinicians.

FIG. 8 is a flowchart illustration of a method for running a simulation of a medical procedure using a hybrid simulation model. In one or more embodiments, the medical procedure is to be performed in a surgical environment, such as the surgical environment 11 of FIG. 1. The method 800 is illustrated in FIG. 8 as a set of operations or processes 802 through 806 and is described with continuing reference to FIGS. 2-5.

Further, the method 800 illustrated in FIG. 8 may be a more detailed method for running a simulation of a medical procedure, as described in process 712 of FIG. 7 above. Not all of the illustrated processes 802 through 806 may be performed in all embodiments of method 800. Additionally, one or more processes that are not expressly illustrated in FIG. 8 may be included before, after, in between, or as part of the processes 802 through 806. In some embodiments, one or more of the processes 802 through 806 may be implemented, at least in part, in the form of executable code stored on non-transitory, tangible, machine-readable media that when run by one or more processors (e.g., the processors of control system) may cause the one or more processors to perform one or more of the processes.

At process 802, the hybrid simulation model 210 is rendered to provide a visualization of the hybrid simulation model 210 on the display system 208. This visualization of the hybrid simulation model 210 may include one or more different views of the hybrid simulation model 210. For example, the visualization may include one or more external views with respect to the patient anatomy 222, one or more internal views with respect to the patient anatomy 222, or a combination thereof.

At process 804, input is detected during the simulation 228 of the medical procedure 202. The input may include any number of inputs. For example, the input may include at least one of user input, a system input received from the medical system 10 of FIG. 1A being used to perform the simulation 228, an input received from the simulation system 200 described in FIG. 2, or some other type of input. The user input may be received from any number of input devices or systems. For example, the user input may be received via the display system 208, a touch screen, a gesture recognition system, a gaze-based recognition system, a speech-based recognition system, an augmented or virtual reality system, a keyboard, a joystick, one or more touch controls, a mouse, some other type of input device, or any combination thereof. In some cases, the user input may be received from the operator input system 16.

In one or more embodiments, a system input received from the medical system 10 may include any number of inputs or input combinations from the assembly 12. For example, the system input may be received from the medical instrument system 14, the endoscopic imaging system 15, or a combination thereof. In one or more embodiments, an input from the simulation system 200 may include an input selected from the dynamic simulation information 230 (e.g., a value of a parameter included in the dynamic simulation information 230), an input from the hybrid simulation model 210, or both.

At process 806, the input is used to update the hybrid simulation model 210 and the dynamic simulation information 230. In one or more embodiments, updating the hybrid simulation model 210 may include modifying a portion of the hybrid simulation model 210, recreating a portion of the hybrid simulation model 210, or both. In some embodiments, updating the dynamic simulation information 230 may include updating the values of one or more parameters included in the dynamic simulation information 230. For example, the input detected at process 804 may represent a simulated movement of the surgical tool 30b shown in FIG. 1B. The movement may be, for example, a deeper insertion of the surgical tool 30b within the patient anatomy 222. The input may be used to, for example, update the instrument position information 502 described in FIG. 5. The updating of the hybrid simulation model 210 and the dynamic simulation information 230 may be performed using any number of or type of algorithms.

At process 808, the visualization of the hybrid simulation model 210 during the simulation 228 of the medical procedure 202 is controlled based on the updated hybrid simulation model 210 and the updated dynamic simulation information 230. In some embodiments, controlling the visualization of the hybrid simulation model 210 means no change in the visualization. For example, the updated hybrid simulation model 210 and the updated dynamic simulation information 230 may not require that the visualization of the hybrid simulation model 210 be changed.

In one or more embodiments, the visualization of the hybrid simulation model 210 is controlled to render the updated hybrid simulation model 210 in a manner that provides the greatest level of fidelity along the operational path (e.g., surgical path) of the medical procedure 202. As one example, the updated instrument position information 502 may cause the portion of the hybrid simulation model 210 being displayed to change. For example, a portion of the hybrid simulation model 210 corresponding to a deeper location within the patient anatomy 222 may be displayed and rendered at a higher level of fidelity compared to its level of fidelity prior to the receiving of the input at process 804.

In one or more embodiments, the simulation system 200 allows the rendering of the hybrid simulation model 210 to be adapted based on the updated dynamic simulation information 230 relevant or corresponding to the current step and/or next step(s) of the medical procedure 202. For example, when the simulation 228 is at a current step in the medical procedure 202, the simulation system 200 may use the dynamic simulation information 230 to make predictions about how the hybrid simulation model 210 is to be rendered or visualized at one or more later steps. Thus, the simulation system 200 may be able to render the portion of the hybrid simulation model 210 corresponding to the one or more next steps more quickly and efficiently once those steps are reached.

At optional process 810, feedback may be optionally provided using an output system. The output system may include, for example, the display system 208, an audio device, a haptic feedback system, a lighting system, or a combination thereof. The audio device may include, for example, without limitation, a speaker system, headphones, an car bud(s), some other type of audio device, or a combination thereof. The feedback may be provided to aid the user (e.g., surgeon or other clinician) during the simulation 228. For example, audio feedback may be used to indicate when a no-pass boundary within the patient anatomy 222 is reached or when the hybrid simulation model 210 and/or the dynamic simulation information 230 indicates that an adverse effect or reaction is being experienced or will be experienced. In some cases, haptic feedback may be used to provide a more realistic experience during the simulation 228. For example, haptic feedback may be used to simulate contact with a hardened mass within patient anatomy 222.

In some cases, at process 810, the visual feedback may include text detailing instructions for performing a current and/or next step of the medical procedure 202. In some embodiments, the visual feedback includes labels, distance information, position information, simulated physiological parameter information, or other types of information. The distance information may include, for example, but not limited to, a distance between a tip of a probe and tissue of the patient 203. The position information may include, for example, but not limited to, a pose of the patient, a position of an instrument or tool, or some other type of positional information. The simulated physiological parameter information may include, for example, a simulated body temperature, a simulated blood pressure, a simulated heart rate, a simulated brain wave, or some other type of simulated physiological parameter value.

Thus, the embodiments provide a simulation system 200 and processes for generating a hybrid simulation model 210 that is customized to a patient 203 and to a medical procedure 202 to be performed on the patient 203 for use in simulating the medical procedure 202. The hybrid simulation model 210 is partially created from patient-specific data 214 and partially created from a generic model 219 of a representative patient. In one or more embodiments, the patient-specific data 214 may be used to scale the generic model 219 and morph only the regions of interest in the generic model 219 that will interact with or be affected by the instruments and/or agents used to perform the medical procedure 202, as well as gravity. Further, the hybrid simulation model 210 may be dynamically adjusted based on dynamic simulation information 230 obtained from running a simulation of the medical procedure 202. The resulting hybrid simulation model 210 enables a high-fidelity virtual reality simulation of the medical procedure 202 to be performed. This type of hybrid simulation model 210 focusing on only the anatomical structures of the patient anatomy 222 of the patient 203 that will interact with or be affected by the instruments and/or agents of the medical procedure 202 may have a reduced size compared to a model that captures the entirety of the patient anatomy 222 with high fidelity. Further, this type of hybrid simulation model 210 may increase the efficiency with which training simulations for performing the medical procedure 202 may be run and stored.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

The invention claimed is:

1. A method for simulating a medical procedure to be performed on a patient, the method comprising:

receiving patient-specific data that is specific to the patient on whom the medical procedure is to be performed;

modifying a generic model using the patient-specific data to generate a hybrid simulation model that is customized to the patient; and performing a simulation of the medical procedure prior to the medical procedure using the hybrid simulation model and dynamic simulation information, wherein the dynamic simulation information includes information about one or more parameters expected to change during the medical procedure and corresponds to at least one of the medical procedure or the patient, wherein the simulation is customized to both the patient and the medical procedure, wherein performing the simulation comprises:

simulating, dynamically, the medical procedure using the hybrid simulation model and the dynamic simulation information such that a patient anatomy of the patient is represented with a gradient of levels of fidelity, wherein a level of fidelity of anatomical structures in the hybrid simulation model decreases during the simulation as a distance from a surgical path of the medical procedure increases.

2. The method of claim 1, wherein performing the simulation comprises:

rendering a first portion of the hybrid simulation model representing a patient anatomy of the patient that interacts with the medical procedure at a level of fidelity that is higher than a level of fidelity at which a second portion of the hybrid simulation model representing the patient anatomy that does not interact with the medical procedure at any step of the medical procedure.

3. The method of claim 1, wherein performing the simulation comprises:

adjusting a visualization of the hybrid simulation model during the simulation to account for effects of simulated interactions between anatomical structures and instruments based on the dynamic simulation information.

4. The method of claim 1, wherein performing the simulation comprises:

rendering the hybrid simulation model to provide a visualization of the hybrid simulation model on a display system;

receiving input during the simulation; and updating the hybrid simulation model and the dynamic simulation information based on the input.

5. The method of claim 4, wherein performing the simulation further comprises:

controlling the visualization of the hybrid simulation model during the simulation of the medical procedure based on the updated hybrid simulation model and the updated dynamic simulation information.

6. The method of claim 1, wherein the dynamic simulation information includes physiological parameter data, instrument position information, field of view information, and patient pose information.

7. The method of claim 1, wherein the patient-specific data includes patient diagnostic data that includes at least one of preoperative imaging data, physical exam data, a geometry of a set of target areas, or a geometry of anatomical structures adjacent to the set of target areas.

8. The method of claim 1, wherein the patient-specific data includes anthropometric data that includes a height measurement, a weight measurement, and anatomical landmark measurements.

9. The method of claim 1, further comprising:

selecting the generic model from a database system, wherein the generic model is of either a representative patient or a representative group of patients.

10. The method of claim 1, wherein the generic model is of a representative patient having anthropometric measurements within a selected range of the patient.

11. The method of claim 1, wherein performing the simulation comprises:

adjusting how one or more anatomical structures of a patient anatomy of the patient deform in response to changes to a pose of the patient during the simulation of the medical procedure.

12. The method of claim 1, wherein performing the simulation comprises:

adjusting a visualization of the hybrid simulation model during the simulation to represent changes in a position of an imaging instrument relative to one or more anatomical structures of a patient anatomy of the patient to assist with training for or rehearsing the medical procedure.

13. The method of claim 1, further comprising:

computing simulation data based on the simulation of the medical procedure.

14. The method of claim 13, further comprising:

modifying the hybrid simulation model based on the simulation data computed to form an updated hybrid simulation model; and modifying the dynamic simulation information based on the simulation data computed to form updated dynamic simulation information.

15. The method of claim 14, further comprising:

performing a new simulation of the medical procedure using the updated hybrid simulation model and the updated dynamic simulation information.

16. The method of claim 1, wherein modifying the generic model using the patient-specific data comprises:

modifying a representation of each of a plurality of anatomical structures in the generic model along a surgical path along which the medical procedure is to be performed based on the patient-specific data received to thereby generate the hybrid simulation model.

17. A simulation system comprising:

a processor configured to:

receive patient-specific data that is specific to a patient on whom a medical procedure is to be performed;

modify a generic model using the patient-specific data to generate a hybrid simulation model that is customized to the patient; and perform a simulation of the medical procedure prior to the medical procedure using the hybrid simulation model and dynamic simulation information, wherein the dynamic simulation information includes information about one or more parameters expected to change during the medical procedure and corresponds to at least one of the medical procedure or the patient, wherein the simulation is customized to both the patient and the medical procedure, wherein performing the simulation comprises:

adjusting how one or more anatomical structures of a patient anatomy of the patient deform in response to changes to a pose of the patient during the simulation of the medical procedure.

18. The simulation system of claim 17, wherein the processor is further configured to dynamically simulate the medical procedure using the hybrid simulation model and the dynamic simulation information to represent a patient anatomy of the patient with a gradient of levels of fidelity, and wherein a level of fidelity of anatomical structures in the hybrid simulation model decreases during the simulation as a distance from a surgical path of the medical procedure increases.

19. The simulation system of claim 17, wherein the processor is further configured to adjust a visualization of the hybrid simulation model during the simulation to account for effects of simulated interactions between anatomical structures and instruments used in the medical procedure based on the dynamic simulation information.

20. The simulation system of claim 17, wherein the dynamic simulation information includes physiological parameter data, instrument position information, field of view information, and patient pose information.

21. The simulation system of claim 17, wherein the patient-specific data includes patient diagnostic data that includes at least one of preoperative imaging data, physical exam data, a geometry of a set of target areas, or a geometry of anatomical structures adjacent to the set of target areas.

22. The simulation system of claim 17, wherein the patient-specific data includes anthropometric data that includes a height measurement, a weight measurement, and anatomical landmark measurements.

23. The simulation system of claim 17, wherein the processor is further configured to retrieve the generic model from a database system and wherein the generic model is of either a representative patient or a representative group of patients.

24. The simulation system of claim 17, wherein the generic model is of a representative patient having anthropometric measurements within a selected range of the patient.

25. The simulation system of claim 17, wherein the processor is further configured to adjust how one or more anatomical structures of a patient anatomy of the patient deform in response to changes to a pose of a patient bed during the simulation of the medical procedure.

26. The simulation system of claim 17, wherein the processor is further configured to adjust a visualization of the hybrid simulation model to represent changes in a location of an endoscope relative to one or more anatomical structures of a patient anatomy of the patient during the simulation of the medical procedure.

27. A method for simulating a medical procedure to be performed on a patient, the method comprising:

receiving anthropometric data and patient diagnostic data for the patient;

selecting a generic model of a representative patient from a database system;

modifying the generic model based on the anthropometric data and the patient diagnostic data to generate a hybrid simulation model that is customized to the patient; and performing a simulation of the medical procedure prior to the medical procedure using the hybrid simulation model and dynamic simulation information, wherein the dynamic simulation information includes information about one or more parameters expected to change during the medical procedure and corresponds to at least one of the medical procedure or the patient, wherein the simulation is customized to both the patient and the medical procedure, wherein the simulation accounts for effects of simulated interactions between anatomical structures of the patient and instruments used in the medical procedure, wherein the simulation dynamically adapts to each step of the medical procedure such that a portion of a patient anatomy of the patient that interacts with the medical procedure at the each step of the medical procedure is rendered at a higher level of fidelity, and wherein performing the simulation comprises:

simulating, dynamically, the medical procedure using the hybrid simulation model and the dynamic simulation information such that a patient anatomy of the patient is represented with a gradient of levels of fidelity, wherein a level of fidelity of anatomical structures in the hybrid simulation model decreases during the simulation as a distance from a surgical path of the medical procedure increases.

* * * * *